(12) United States Patent
Sunagawa et al.

(10) Patent No.: US 6,428,482 B1
(45) Date of Patent: Aug. 6, 2002

(54) CENTRAL-ARTERY-PRESSURE-WAVEFORM ESTIMATING APPARATUS

(75) Inventors: Kenji Sunagawa, Ibaraki; Masaru Sugimachi, Suita, both of (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/810,214

(22) Filed: Mar. 19, 2001

(30) Foreign Application Priority Data

Aug. 11, 2000 (JP) ........................................ 2000-244876

(51) Int. Cl.[7] ................................................. A61B 5/02
(52) U.S. Cl. ........................................ 600/485; 600/490
(58) Field of Search ................................ 600/485, 490, 600/500–503

(56) References Cited

U.S. PATENT DOCUMENTS

| | | | | |
|---|---|---|---|---|
| 5,301,675 A | * | 4/1994 | Tomita | 600/485 |
| 5,603,329 A | * | 2/1997 | Hosaka et al. | 600/493 |
| 6,193,669 B1 | * | 2/2001 | Degany et al. | 600/486 |
| 6,280,390 B1 | * | 8/2001 | Akselrod et al. | 600/485 |

FOREIGN PATENT DOCUMENTS

JP 10-094526 4/1998

OTHER PUBLICATIONS

Sterigopulos et al., Physical basis of pressure transfer from periphery to aorta: a model–based study. American Journal of Physiology 1998; 274; H1386–H1392.

Karamanoglu et al., On–line synthesis of the human ascending aortic pressure pulse from the finger pulse. Hypertension. 1997; 30; 1416–1424.

Westerhof et al., Forward and backward waves in the arterial system. Cardiovasc Res 1972; 6: 648–656.

Sugimachi et al., Estimation of arterial mechanical properties from aortic and tonometric arterial pressure waveforms. Methods Inf Med 1997; 36: 250–253.

* cited by examiner

Primary Examiner—Robert L. Nasser
Assistant Examiner—Patricia Mallari
(74) Attorney, Agent, or Firm—Oliff & Berridge, PLC

(57) ABSTRACT

An apparatus for non-invasively estimating a waveform of a blood pressure in a central artery, including a detecting device which non-invasively detects a pressure pulse wave from a first portion of a peripheral artery, a first determining device for determining, according to a vascular-system model, a difference between a blood pressure at the first portion of the peripheral artery and a blood pressure at an end of the same, based on the detected pressure pulse wave, a first estimating device for estimating, based on the detected pressure pulse wave and the determined difference, a waveform of a forward pressure pulse wave at the first portion and a waveform of a backward pressure pulse wave at the first portion, a second determining device for determining a propagation time in which the pressure pulse wave propagates from a second portion of the central artery to the first portion of the peripheral artery, and a second estimating device for estimating, based on the respective estimated waveforms of the forward and backward pressure pulse waves and the determined propagation time, a waveform of a forward pressure pulse wave at the second portion and a waveform of a backward pressure pulse wave at the second portion, and estimating a waveform of a blood pressure at the second portion by adding the respective estimated waveforms of the forward and backward pressure pulse waves at the second portion.

8 Claims, 11 Drawing Sheets

FIG. 9A
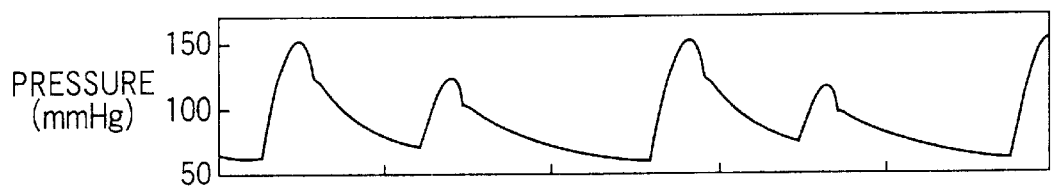
FIG. 9B
FIG. 9C PRIOR ART
FIG. 9D INVENTION
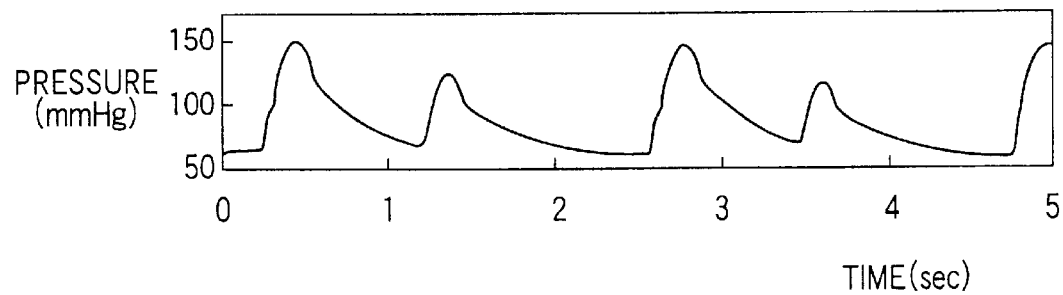

INVENTION

CENTRAL-ARTERY-PRESSURE-WAVEFORM ESTIMATING APPARATUS

BACKGROUND OF THE INVENTION

1. Field of the Invention

The present invention relates to an apparatus for non-invasively estimating the waveform of blood pressure in a central artery (e.g., an aortic artery or a carotid artery) of a living subject.

2. Discussion of Related Art

There is known a blood-pressure (BP) estimating device which continuously estimates, by so-called tonometry, BP of a living subject, such as a patient under a surgical operation, to monitor his or her BP. The BP estimating device includes a pressure-pulse-wave (PPW) sensor which is pressed via skin against a peripheral artery, such as a radial artery, to detect a peripheral PPW from the artery, and continuously estimates the BP of the subject based on the detected peripheral PPW.

However, the waveform of the peripheral PPW detected by the PPW sensor differs from the waveform of blood pressure in a central artery, in that the waveform of peripheral PPW is distorted as compared with the waveform of central-artery pressure and is time-wise delayed from the same. Therefore, if the waveform of central-artery pressure is continuously estimated based on the waveform of peripheral PPW by the BP estimating device, then it would be necessary to correct the waveform of peripheral PPW in an appropriate manner.

There has been proposed a method of correcting the distortion of the waveform of peripheral PPW to estimate continuously the waveform of central aortic pressure (i.e., blood pressure at the heart-side end of aorta) as a sort of central-artery pressure. This method includes determining an average transfer function between the waveform of central aortic pressure and the waveform of peripheral PPW, and correcting the continuously detected peripheral PPW based on the transfer function. In addition, there has been also proposed a method of estimating the waveform of central aortic pressure by (a) separating the waveform of peripheral PPW into an estimated waveform of forward PPW and an estimated waveform of backward PPW, (b) estimating, based on the estimated waveforms of forward and backward PPWs and a propagation time in which the PPW propagates between the heart-side end of aorta and a portion of the peripheral artery against which the PPW sensor is pressed, the respective waveforms of forward and backward PPWs at the heart-side end of aorta, and (c) estimating the waveform of central aortic pressure by adding the estimated waveforms of forward and backward PPWs at the heart-side end of aorta. (Stergiopulos N, Westerhof B E, Westerhof N: Physical basis of pressure transfer from periphery to aorta; a model-based study. American Journal of Physiology 1998; 274; H1386–H1392).

However, since the above-indicated former or first method needs complex calculations including Fourier transformation and/or convolution integration, it is difficult to monitor the waveform of central aortic pressure on a real-time basis. In addition, though the latter or second method can accurately estimate, by simple calculations, the waveform of central aortic pressure, it has the disadvantage that it needs to measure blood flow in the peripheral artery.

Moreover, there has been proposed a third method of determining a transfer function based on a vascular-system model, and estimating the waveform of central aortic pressure based on the transfer function and BP measured from a finger. (Karamanoglu M, Feneley M P: On-line synthesis of the human ascending aortic pressure pulse from the finger pulse. Hypertension. 1997; 30; 1416–1424).

However, the third method has the disadvantage that it needs a parameter which can be measured in an invasive manner only.

SUMMARY OF THE INVENTION

It is therefore an object of the present invention to provide an apparatus which can estimate, with each and accuracy, a waveform of blood pressure in a central artery of a living subject.

The above object has been achieved by the present invention, which provides an apparatus for non-invasively estimating a waveform of a blood pressure in a central artery of a living subject, comprising a pressure-pulse-wave detecting device which includes a pressure-pulse-wave sensor adapted to be pressed, via a skin of the subject, against a first portion of a peripheral artery located on a downstream side of the central artery and which non-invasively detects, through the pressure-pulse-wave sensor, a pressure pulse wave produced from the first portion of the peripheral artery; a blood-pressure-difference determining means for determining, according to a predetermined vascular-system model, a blood-pressure difference between a blood pressure at the first portion of the peripheral artery pressed by the pressure-pulse-wave sensor and a blood pressure at an end of the peripheral artery, based on the pressure pulse wave detected by the pressure-pulse-wave detecting device; a peripheral-artery-blood-pressure-waveform estimating means for estimating, based on the pressure pulse wave detected by the pressure-pulse-wave detecting device and the blood-pressure difference determined by the blood-pressure-difference determining means, a waveform of a forward pressure pulse wave at the first portion of the peripheral artery pressed by the pressure-pulse-wave sensor, and a waveform of a backward pressure pulse wave at the first portion of the peripheral artery; a propagation-time determining means for determining a propagation time in which the pressure pulse wave propagates from a second portion of the central artery to the first portion of the peripheral artery; and a central-artery-blood-pressure-waveform estimating means for estimating, based on the respective waveforms of the forward and backward pressure pulse waves estimated by the peripheral-artery-blood-pressure-waveform estimating means and the propagation time determined by the propagation-time determining means, a waveform of a forward pressure pulse wave at the second portion of the central artery and a waveform of a backward pressure pulse wave at the second portion of the central artery, and estimating a waveform of a blood pressure at the second portion of the central artery, by adding the respective estimated waveforms of the forward and backward pressure pulse waves at the second portion of the central artery.

In the present apparatus, the blood-pressure-difference determining means determines, according to the predetermined vascular-system model, the blood-pressure difference between the blood pressure at the first portion of the peripheral artery pressed by the pressure-pulse-wave sensor and the blood pressure at the end of the peripheral artery, based on the pressure pulse wave non-invasively detected by the pressure-pulse-wave detecting device. In addition, the peripheral-artery-blood-pressure-waveform estimating means estimates, based on the pressure pulse wave detected by the pressure-pulse-wave detecting device and the blood-pressure difference determined by the blood-pressure-difference determining means, the waveform of forward pressure pulse wave at the first portion of the peripheral artery, and the waveform of backward pressure pulse wave at the first portion of the peripheral artery, and the central-artery-blood-pressure-waveform estimating means estimates, based on the respective waveforms of the forward and backward pressure pulse waves and the propagation time determined by the propagation-time determining means, the waveform of blood pressure in the central artery. Thus, the present apparatus can easily estimate the waveform of blood pressure in the central artery, by just detecting the pressure pulse wave from the peripheral artery and measuring the propagation time.

BRIEF DESCRIPTION OF THE DRAWINGS

The above and other objects, features, advantages and technical and industrial significance of the present invention will be better understood by reading the following detailed description of preferred embodiments of the invention, when considered in connection with the accompanying drawings, in which:

FIG. 9A is a graph showing a CAP waveform detected using a catheter;

FIG. 9B is a graph showing a radial-artery pressure waveform detected using the PPW detecting probe;

FIG. 9C is a graph showing a CAP waveform estimated from the detected radial-artery pressure waveform by a conventional method using a transfer function; and FIG. 9D is a graph showing a CAP waveform estimated from the detected radial-artery pressure waveform in the invention method using the vascular-system model of FIG. 7;

DETAILED DESCRIPTION OF PREFERRED EMBODIMENTS

Hereinafter, there will be described an embodiment of the present invention, by reference to the accompanying drawings.

Figure 1:
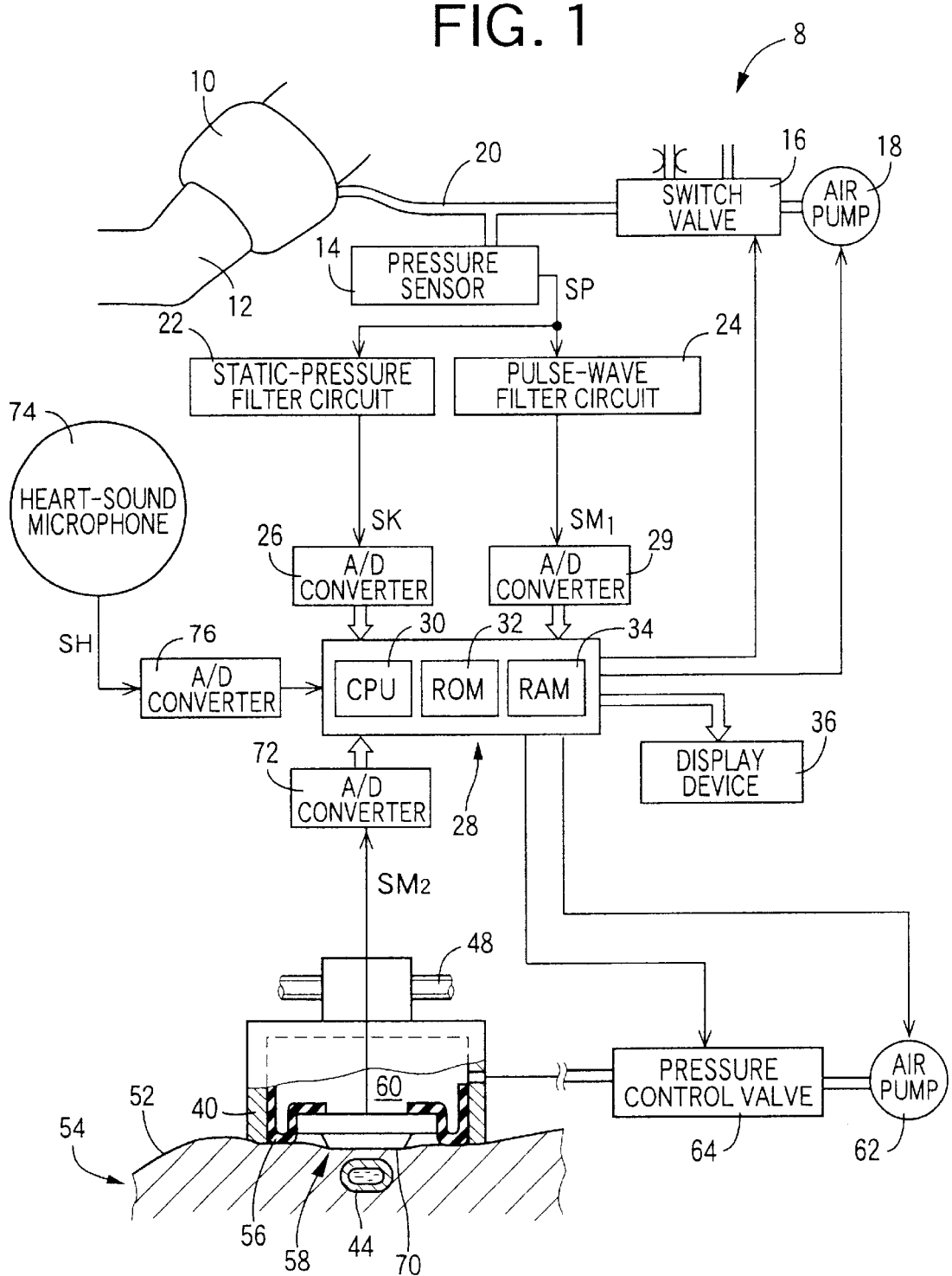
FIG. 1 is a diagrammatic view of the construction of a central-aortic-pressure (CAP) waveform estimating apparatus to which the present invention is applied.

FIG. 1 is a diagrammatic view for explaining a construction of a central-aortic-pressure (CPA) waveform estimating apparatus 8 to which the present invention is applied. The CAP-waveform estimating apparatus 8 estimates a CAP waveform of a living subject as a sort of central-artery blood-pressure waveform. The CAP-waveform estimating apparatus 8, shown in FIG. 1, also functions as a non-invasive and continuous blood-pressure (BP) estimating apparatus which non-invasively and continuously estimates BP values of the subject.

In FIG. 1, the CAP-waveform estimating apparatus 8 includes an inflatable cuff 10 which includes a rubber bag and a belt-like cloth bag in which the rubber bag is accommodated. The cuff 10 is wound around, e.g., an upper arm 12 of a patient as a living subject. The waveform estimating apparatus 8 additionally includes a pressure sensor 14, a switch valve 16, and an air pump 18 which are connected to the cuff 10 via piping 20. The switch valve 16 is selectively placed in three states, that is, a pressure-supply state in which the valve 16 allows pressurized air to be supplied from the air pump 18 to the cuff 10, a slow-deflation state in which the valve 16 allows the pressurized air to be slowly deflated from the cuff 10, and a quick-deflation state in which the valve 16 allows the pressurized air to be quickly deflated from the cuff 10.

The pressure sensor 14 detects an air pressure in the cuff 10, and supplies a pressure signal, SP, representing the detected pressure, to a static-pressure filter circuit 22 and a pulse-wave filter circuit 24. The static-pressure filter circuit 22 includes a low-pass filter which selects, from the pressure signal SP, a cuff-pressure signal, SK, representing a static pressure, Pc, contained in the pressure represented by the pressure signal SP. The cuff-pressure signal SK is supplied to an electronic control device 28 via an analog-to-digital converter ("A/D") converter 26.

The pulse-wave filter circuit 24 includes a band-pass filter which selects, from the pressure signal SP, a pulse-wave signal, $SM_1$, representing oscillatory components contained in the pressure represented by the pressure signal SP, that is, a cuff pulse wave produced in the cuff 10. The pulse-wave signal $SM_1$ is supplied to the control device 28 via an A/D converter 30. The cuff pulse wave represented by the pulse-wave signal $SM_1$ is an oscillatory pressure wave that is produced from a brachial artery (not shown) of the patient in synchronism with the heartbeat of the patient and is transmitted to the cuff 10 worn on the upper arm 12 of the patient. Thus, the cuff 10, the pressure sensor 14, and the pulse-wave filter circuit 24 cooperate with one another to provide a cuff-pulse-wave sensor.

The control device 28 is provided by a microcomputer including a central processing unit (CPU) 30, a read only memory (ROM) 32, a random access memory (RAM) 34, and an I/O port (not shown). The CPU 30 processes, according to control programs pre-stored in the ROM 32, input signals while utilizing a temporary-storage function of the RAM 34, and outputs, via the I/O port, drive signals to the switch valve 16 and the air pump 18 to control the same 16, 18. In addition, the control device 30 controls a display device 36 to display various sorts of information.

Figure 2:
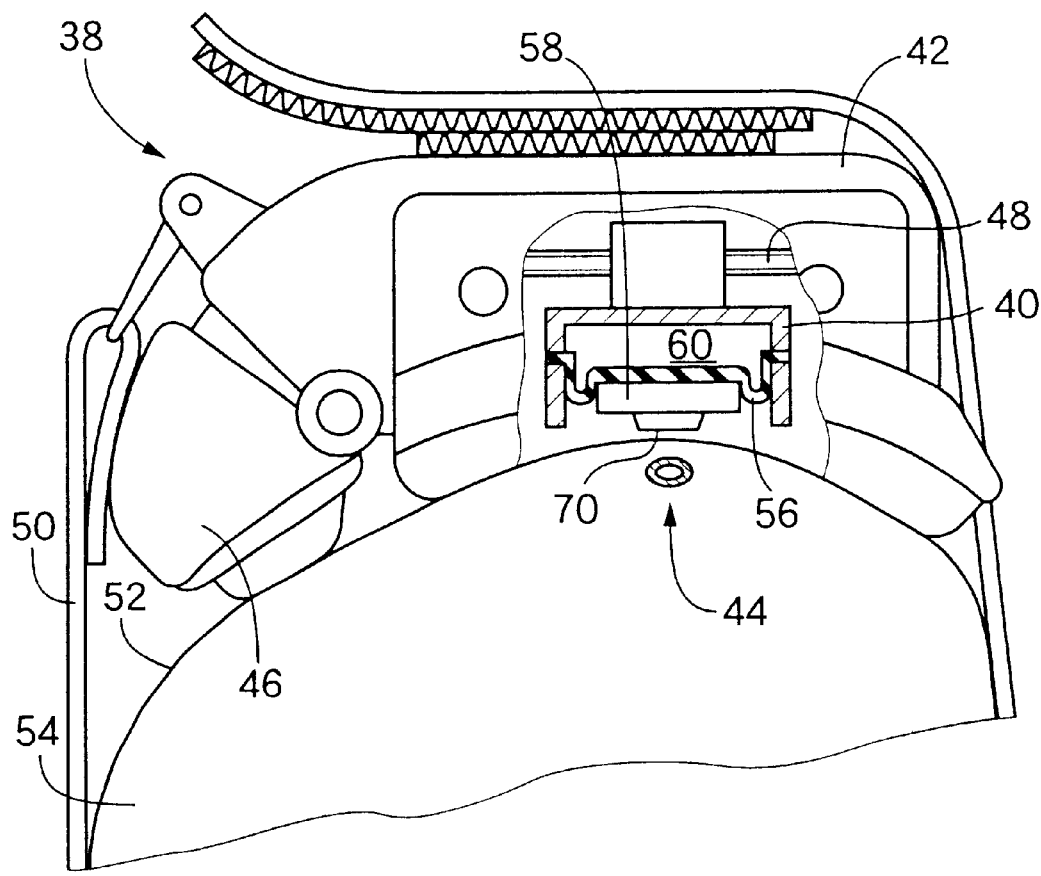
FIG. 2 is an enlarged view of a pressure-pulse-wave (PPW) detecting probe of the apparatus of FIG. 1, with a portion of the probe being removed.

A pressure-pulse-wave detecting probe 38 as a pressure-pulse-wave detecting device detects a pressure pulse wave produced from a peripheral artery of the patient, i.e., an artery located on a downstream side of a central artery of the patient. As illustrated in detail in FIG. 2, the probe 38 includes a casing 42 which accommodates a housing 40 having a container-like shape; and a feed screw 48 which is threadedly engaged with the housing 40 and is rotated by an electric motor (not shown) provided in a drive section 46 of the casing 42, to move the housing 40 in a widthwise direction of a radial artery 44. A fastening band 50, attached to the casing 42, is used to wear the casing 42 on a wrist 54 of a left arm of the subject that is opposite to the right arm on which the cuff 10 is worn, such that an open end of the container-like housing 40 is opposed to a body surface 52 of the patient. The housing 40 accommodates a pressure-pulse-wave (PPW) sensor 58 via an elastic diaphragm 56, such that the PPW sensor 58 is movable relative to the housing 40 and is advanceable out of the open end of the housing 40. The elastic diaphragm 56 defines an airtight, pressure chamber 60 in the back of the PPW sensor 58. The diaphragm 40 is formed of a thin elastic sheet. The pressure chamber 60 is supplied with pressurized air from an air pump 62 via a pressure-control valve 64, so that the PPW sensor 58 is pressed against the body surface 52 with a pressing force corresponding to the air pressure in the chamber 60.

The housing 40 and the diaphragm 56 cooperate with each other to provide a pressing device 66 which presses the PPW sensor 58 against the radial artery 44 via the body surface or skin 52. The pressing device 66 presses the PPW sensor 58 with an optimum pressing force, $P_{HDPO}$, described later. The feed screw 48 and the electric motor (not shown) cooperate with each other to provide a press-position changing device or a widthwise moving device which changes a press position where the PPW sensor 58 is pressed, by moving the sensor 58 in the widthwise direction of the artery 44.

Figure 3:
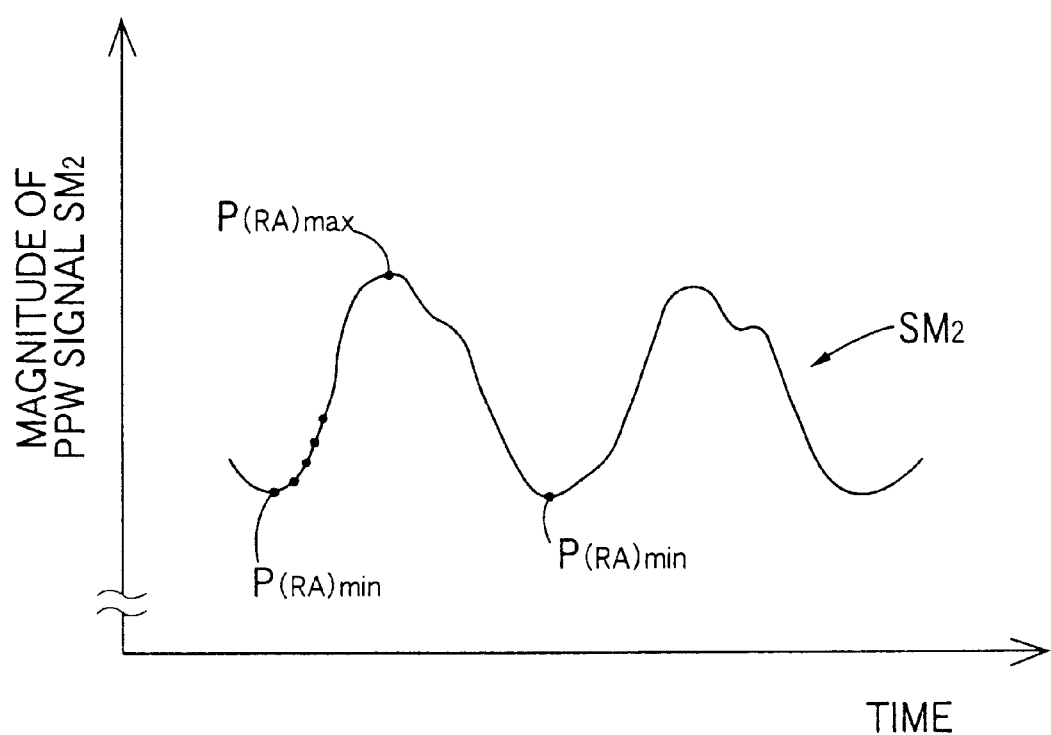
FIG. 3 is a view showing a pressure pulse wave (PPW) represented by a PPW signal supplied by a PPW sensor of the PPW detecting probe FIG. 2.

The PPW sensor 58 has a press surface 70 which is provided by, e.g., a semiconductor chip such as a monocrystalline silicon, and has, in the pressure surface 70, a number of semiconductor pressure-sensing elements E (not shown) which are arranged at a regular interval (e.g., 0.2 mm) of distance in the widthwise direction of the radial artery 44, i.e., in a direction which is parallel to the feed screw 48 and in which the PWB 58 is moved. In a state in which the PWB sensor 58 is pressed against the radial artery 44 via the body surface 52 of the wrist 54, each of the pressure-sensing elements detects a pressure pulse wave (PPW), $P_{(RA)}$, i.e., an oscillatory pressure wave which is produced from the radial artery 44 and is transmitted to the body surface 52, and supplies a PPW signal, $SM_2$, representing the detected PPW $P_{(RA)}$, to the control device 28 via an A/D converter 72. FIG. 3 shows a waveform of the PPW $P_{(RA)}$ represented by the PPW signal $SM_2$ produced by one of the pressure-sensing elements of the PPW sensor 58.

The present CAP-waveform estimating apparatus 8 additionally includes a heart-sound microphone 74 which is placed or worn at a predetermined position on the chest of the subject, to detect hear sounds produced from the heart of the subject, and outputs a heart-sound signal, SH, representing the detected heart sounds. The heart-sound signal SH produced by the heart-sound microphone 74 is supplied to the control device 28 via an analog-to-digital (A/D) converter 76. The heart sounds detected by the microphone 74 includes a first heart sound I which is produced when the aortic valve opens. When the aortic valve opens, an aortic pulse wave is produced. Thus, the heart-sound signal SH representing the heart sounds provides a first signal which is produced in synchronism with the aortic pulse wave at the heart-side end of the aorta; and the heart-sound microphone 74 provides a first sensor which detects the first signal.

Figure 4:
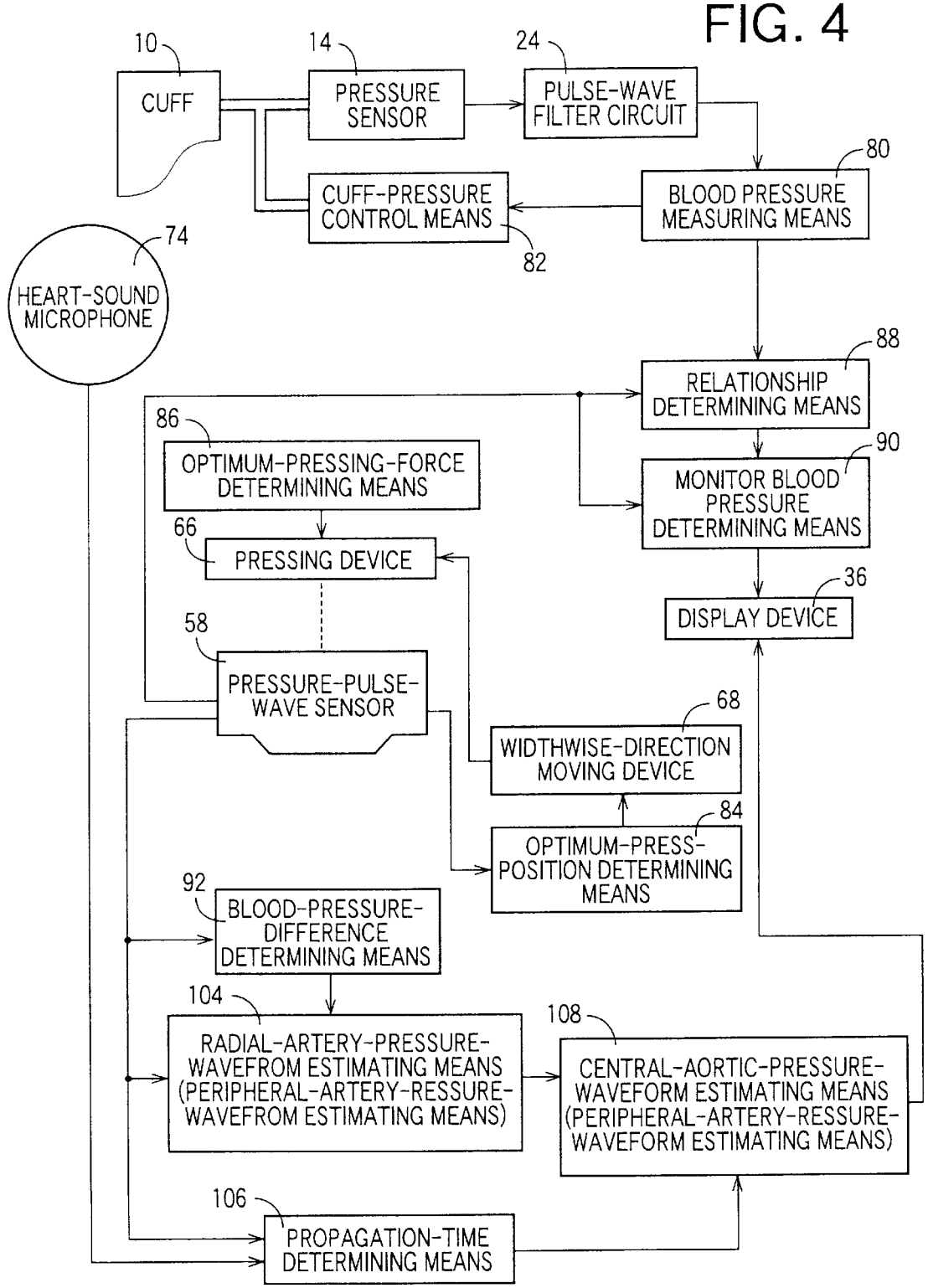
FIG. 4 is a diagrammatic view of relevant control functions of a control device of the apparatus of FIG. 1.

FIG. 4 is a diagrammatic view for explaining various functions of the control device 28 of the CAP-waveform estimating apparatus 8 constructed as described above.

A cuff-pressure control means 82 quickly increases the pressing pressure of the cuff 10 wound around the upper arm of the patient, up to a target pressure, PCM, (e.g., 180 mmHg) and then slowly decreases the cuff pressure at the rate of 3 mmHg/sec. During this slow deflation of the cuff 10, a blood-pressure (BP) measuring means 80 collects a plurality of heartbeat-synchronous pulses represented by the pulse-wave signal $SM_1$ obtained from the cuff 10 via the pressure sensor 14 and the pulse-wave filter circuit 24, calculates respective amplitudes of the collected pulses, and determines, in well-known oscillometric method, a systolic BP value, $BP_{SYS}$, a mean BP value, $BP_{MEAN}$, and a diastolic BP value, $BP_{DIA}$, of the subject based on the variation of the amplitudes of the collected pulses. The thus determined BP values $BP_{SYS}$, $B_{MEAN}$, $BP_{DIA}$ are displayed on the display device 36.

An optimum-pressing-position determining means 84 carries out a press-position changing operation, when a prescribed press-position changing condition is satisfied. The press-position changing condition is that one of the pressure-sensing elements, E, arranged in array in the press surface 70 which one element is a maximum-amplitude detecting element (i.e., an active element), $E_O$, is positioned within a predetermined number of elements counted from each of opposite ends of the array of elements E, or within a predetermined distance inward from the each end. This condition may be satisfied when the PPW detecting probe 38 is initially worn on the wrist 54 of the patient. The press-position changing operation includes moving the PPW sensor 58 away from the body surface 52, operating the widthwise-direction moving device 68 to move the pressing device 66 and the PPW sensor 58 relative to the radial artery 44 by a predetermined incremental distance, and operating the pressing device 66 to press the sensor 58 against the surface 52 with a considerably small, first hold-down pressure, $HDP_1$. In this state, it is judged whether the press-position changing condition is satisfied again. The press-position changing operation and the judging operation are continued or repeated till the PPW sensor 58 is brought into a state in which the press-position changing condition is not satisfied, more preferably, till the active element $E_O$ is positioned or found at substantially the center of the array of elements E. Thus, the PPW sensor 58 is positioned at an optimum press position relative to the radial artery 44.

Figure 5:
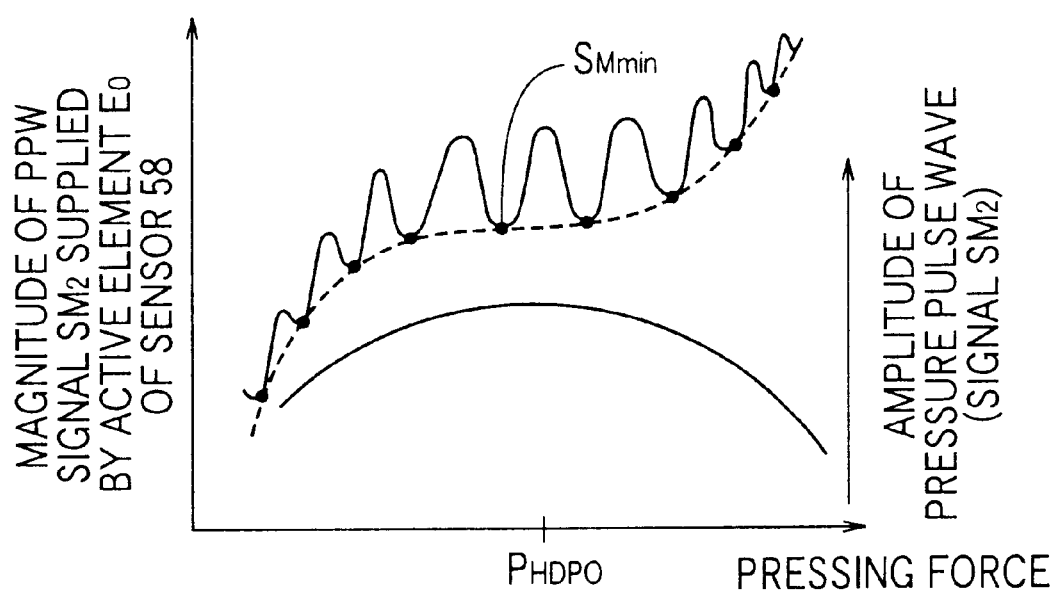
FIG. 5 is a view for explaining a manner in which an optimum pressing force is determined by an optimum-pressing-force determining means of the apparatus of FIG. 1.

An optimum-pressing-force determining means 86 continuously changes the pressing force applied to the PPW sensor 58 positioned at the optimum press position, within a sufficiently wide force range. During this pressing-force change, the determining means 86 continuously obtains the pressure pulse wave $P_{(RA)}$ or the pulse-wave signal $SM_2$ detected by the above-indicated active pressure-sensing element $E_O$ of the PPW sensor 58, determines, based on the continuously obtained pressure pulse wave $P_{(RA)}$, an optimum pressing force $P_{HDPO}$, and presses the PPW sensor 58 against the radial artery 44, with the determined optimum pressing force $P_{HDPO}$. The optimum pressing force $P_{HDPO}$ is so determined as to fall, as shown in FIG. 5, within a pressure range whose center corresponds to the greatest one of respective pulse amplitudes (indicated at solid line) of the pulse-wave signal $SM_2$ detected during the pressing-force change. Alternatively, the optimum force $P_{HDPO}$ may be so determined as to fall, as shown in FIG. 5, within a pressure range whose center corresponds to the center of a flat portion of a curve (indicated at broken line) connecting the respective minimum magnitudes, $S_{Mmin}$, of heartbeat-synchronous pulses of the pulse-wave signal SM2 detected during the pressing-force change.

Figure 6:
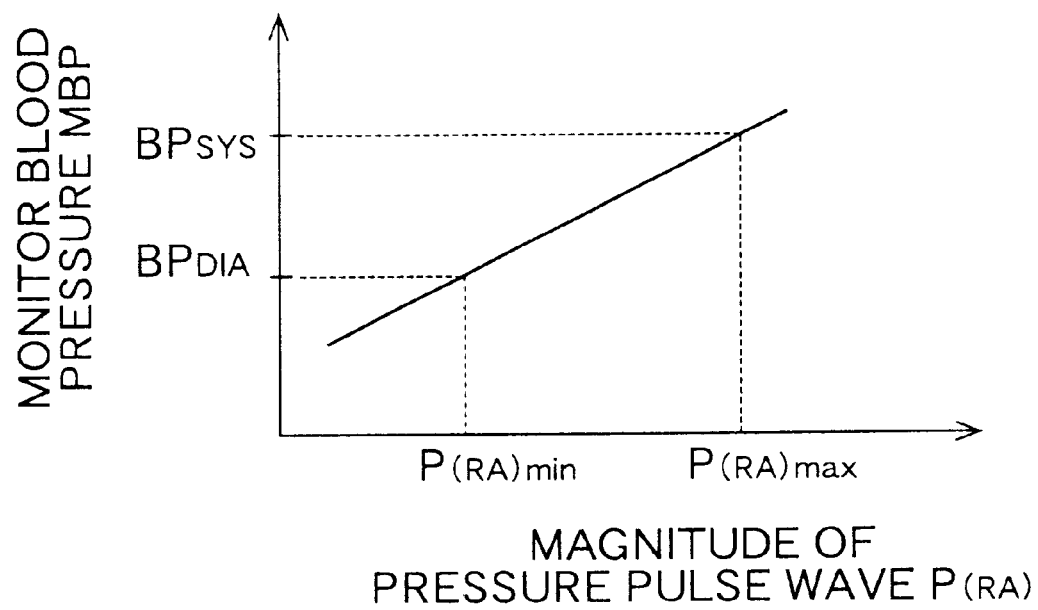
FIG. 6 is a view for explaining a relationship which is determined by a relationship determining means of the apparatus of FIG. 1.

A relationship determining means 88 periodically determines, as shown in FIG. 6, a relationship between monitor BP, MBP, and magnitude of pressure pulse wave (i.e., magnitude of pulse-wave signal $SM_2$), based on the BP values measured by the BP measuring means 80 and the pressure pulse wave $P_{(RA)}$, i.e., the pulse-wave signal $SM_2$ detected by the active element $E_O$ of the PPW sensor 58. The relationship shown in FIG. 6 is expressed by the following expression (1):

$$MBP = A \cdot P_{(RA)} + B \quad (1)$$

where A and B are constants.

A monitor-blood-pressure (MBP) determining means 90 successively or consecutively determines, according to the above relationship, at least one of a monitor systolic BP value, $MBP_{SYS}$, a monitor mean BP value, $MBP_{MEAN}$, and a monitor diastolic BP value, $MBP_{DIA}$, based on at least one of a maximum magnitude, $S_{(RA)max}$, a mean magnitude, and a minimum magnitude $S_{(RA)min}$ of each of successive heartbeat synchronous pulses of the pressure pulse wave $P_{(RA)}$, i.e., the pulse-wave signal $SM_2$ detected by the active element $E_O$ of the PPW sensor 58. The thus determined monitor BP value or values MBP is or are successively displayed on the display device 36.

Figure 7:
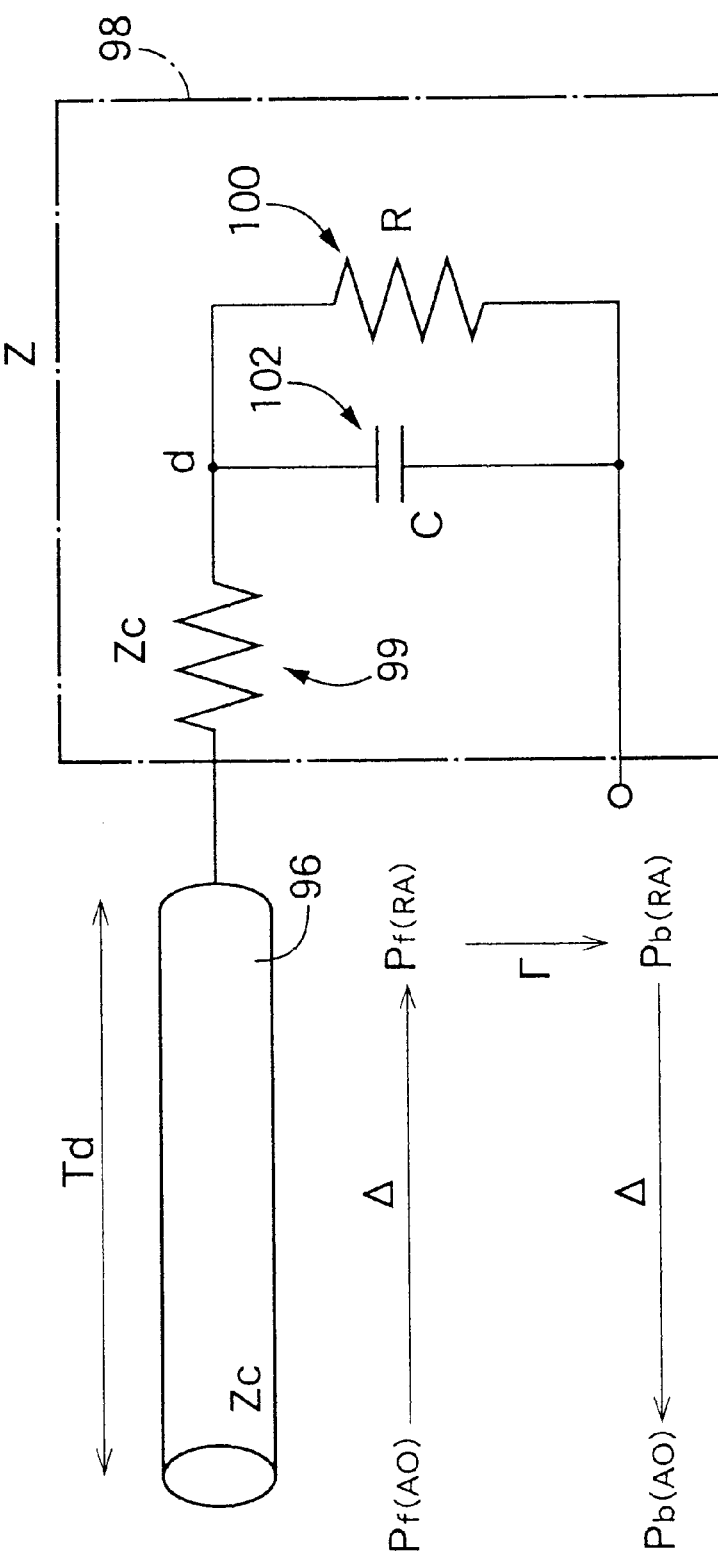
FIG. 7 is a view for explaining a model of a vascular system of a human being that is employed in the apparatus of FIG. 1.

A BP-difference determining means 92 continuously calculates, according to a predetermined vascular-system model 94 (FIG. 7), a BP difference, A, between a BP value $P_{(RA)}$ at the portion of the radial artery 44 that is pressed by the PPW sensor 58, and a BP value, Pd, at the end of the radial artery 44, based on the magnitude (i.e., the BP value $P_{(RA)}$) of the pressure pulse wave $P_{(RA)}$ (FIG. 3) continuously detected by the sensor 58. The vascular-system model 94, shown in FIG. 7, models a vascular system of the subject. In the model 94, a tube 96 is elastic and exhibits no pressure loss, and corresponds to an artery from the aorta (i.e., the central artery) to the portion of the radial artery 44 (i.e., the peripheral artery) pressed by the PPW sensor 58. The tube 96 has a characteristic impedance, Zc. A peripheral circuit 98 is connected to the peripheral end of the tube 96, and models a portion of the vascular system that is located on a peripheral side of the portion of the radial artery 44 pressed by the PPW sensor 58. The peripheral circuit 98 includes a resistor 99 which represents a portion of the radial artery 44 that is located between the portion thereof pressed by the PPW sensor 58 and the peripheral end thereof; and a resistor, R, 100 and a capacitor, C, 102 each of which is connected in series to the resistor 99 and which are connected in parallel to each other. The resistor 99 has the same impedance with that Zc of the tube 96, because generally the impedance of a blood vessel is defined by the diameter, elasticity and wall thickness thereof and the physical properties of blood and these variables do not largely change between respective portions of the vessel (i.e., the radial artery 44) on upstream and downstream sides of the PPW sensor 58.

The above-indicated BP difference A can be expressed as the product, $A = Zc \times Q_{(RA)}$, of the characteristic impedance Zc of the resistor 99 and an amount, $Q_{(RA)}$, of blood that flows in the tube 96. In addition, a relationship between (a) the BP difference, A(t), at a time, t, (b) the pressure at the peripheral end of the tube 96 at the time t, i.e., the pulse pressure, $P_{(RA)}(t)$, at the portion of the radial artery 44 pressed by the PPW sensor 58 at the time t, and (c) the pressure, Pd(t), at the peripheral end, i.e., point d, of the radial artery 44 can be expressed as follows:

$$A(t) = P_{(RA)}(t) - Pd(t) \quad (2)$$

In addition, since the amount of blood that flows into the capacitor 102 can be expressed as A(t)/Zc, and the amount of blood that flows out of the capacitor 102 can be expressed as Pd(t)/R, an amount of electric charge that is charged into the capacitor 102 in a sufficiently short, predetermined time, T, (e.g., 1 msec) can be expressed as follows:

$$\{A(t)/Zc - Pd(t)/R\} \times T \quad (3)$$

The quotient obtained by dividing the above expression (3) by the capacitance C of the capacitor 102 means a voltage increase which is newly produced between the opposite ends of the capacitor 102 in the predetermined time T. Therefore, a voltage, Pd(t+T), at the point d after the time T can be expressed as follows:

$$Pd(t+T) = Pd(t) + \{A(t)/Zc/C - Pd(t)/R/C\} \times T = Pd(t) + \{A(t)/(Zc/R)/(C \cdot R) - Pd(t)/(C \cdot R)\} \times T \quad (4)$$

The above unknown values Zc/R and C·R can be determined as follows: First, an actual central-aortic pressure waveform, $P_{(AO)}$, and an actual radial-arterial pressure waveform, $P_{(RA)}$, are measured, and an actual transfer function is determined based on the two waveforms $P_{(AO)}$, $P_{(RA)}$. This method is described in detail by Sugimachi et al. (Methods Inf Med 1997). In addition, a transfer function, H($\omega$), corresponding to the vascular-system model 94 can be expressed as follows:

$$H(\omega) = (1 + \Delta^2 \Gamma)/(\Delta + \Delta \Gamma) \quad (5)$$

where $\omega$ is an angular frequency, $\Delta$ is a delay element, $\Delta = -\omega \cdot Td \cdot j$, $\Gamma = (Z - Zc)/(Z + Zc)$ (Z is the impedance of the peripheral circuit 98).

Therefore, the unknown values Zc/R and C·R can be determined as the combination of parameters which assure that the transfer function H($\omega$) most faithfully represents, in the range of 0 to 8 Hz, the actually measured transfer function. However, in the present embodiment, a constant value (e.g., an average value) which is determined based on each of the thus determined values Zc/R and C·R is employed. The average value is determined based on respective values Zc/R or C·R obtained from a number of living subjects. The reasons why the constant values Zc/R, C·R can be employed are that experiments show that though the respective values Zc/R, C·R may more or less differ among the subjects, the finally obtained central aortic pressure values $P_{(AO)}$ are not influenced so greatly, and that the calculations needed are simplified by using the constant values. In addition, in order to determine the current value Pd(t+T) from the above expression (4), it is needed to give an initial value to the variable Pd(t). A constant value, e.g., an average value of the peripheral-artery pressure, i.e., an average value of the radial-artery pressure $P_{(RA)}$ detected by the PPW sensor 58, is given as the initial value of the variable Pd(t). Thus, the variable Pd(t) and accordingly the variable A(t) can be continuously determined by replacing, in the expressions (2) and (4), the values Zc/R, C·R with the thus obtained constants, and giving the thus obtained constant initial value to the variable Pd(t). Since a constant value is given as the initial value of the variable Pd(t), the obtained values Pd(t), A(t) are not accurate in a very initial period. However, the values Pd(t), A(t) will approach accurate values as the expressions (2) and (4) are repetitively used.

A radial-artery-pressure-waveform estimating means 104 as a peripheral-artery-pressure-waveform estimating means continuously estimates, according to the following expressions (6) and (7), a waveform, $P_{f(RA)}(t)$, of a forward pressure pulse wave and a waveform, $P_{b(RA)}(t)$, of a backward pressure, each at the portion of the radial artery 44 pressed by the PPW sensor 58, based on the pressure pulse wave $P_{(RA)}(t)$, continuously detected by the sensor 58 and the BP difference A(t) continuously determined by the means 92:

$$P_{f(RA)}(t)=(P_{(RA)}(t)+A(t))/2 \qquad (6)$$

$$P_{b(RA)}(t)=(P_{(RA)}(t)-A(t))/2 \qquad (7)$$

The above expressions (6), (7) are known as those which can be used to estimate, based on a pressure pulse wave $P_{(RA)}$ and a blood flow wave $Q_{(RA)}$, a waveform $P_{f(RA)}(t)$ of a forward pressure pulse wave and a waveform $P_{b(RA)}(t)$ of a backward pressure, each of that pressure pulse wave $P_{(RA)}$. (Westerhof N, Sipkema P, Bos G C van, Elzinga G: Forward and backward waves in the arterial system. Cardiovasc Res 1972; 6: 648–656).

A propagation-time determining means 106 successively determines, as a propagation time Td, a time difference between a time when the first sensor detects a predetermined characteristic point of each first heartbeat-synchronous signal successively produced from the predetermined portion of the central artery, and a time when the PPW sensor 58 detects a predetermined characteristic point of the pressure pulse wave $P_{(RA)}$ that corresponds to the predetermined characteristic point of the first pulse-synchronous signal. Since, in the present apparatus 8, the heart-sound microphone 74 functions as the first sensor, the means 106 successively determines, as the propagation time Td, the time difference between the minimum-magnitude point of each first heart sound I successively detected by the microphone 74 and the minimum-magnitude point of each heartbeat-synchronous pulse successively detected by the PPW sensor 58.

A central-aortic-pressure (CAP) waveform estimating means 108 as a central-artery-pressure-waveform estimating means continuously estimates, based on the forward-pressure-pulse-wave waveform $P_{f(RA)}$ and the backward-pressure-pulse-wave waveform $P_{b(RA)}$ continuously estimated by the means 104 and the propagation time Td successively determined by the means 106, a waveform, $P_{(AO)}$, of central aortic pressure in a manner described below, and continuously displays the thus estimated central aortic pressure waveform $P_{(AO)}$ on a predetermined portion of the screen image of the display device 36. According to the vascular-system model 94, the forward-pressure-pulse-wave waveform $P_{f(RA)}$ estimated for the radial artery 44 has the same shape as that of forward-pressure-pulse-wave waveform $P_{f(AO)}$ at the heart-side end of the aorta but is delayed from the same by the propagation time Td; and the backward-pressure-pulse-wave waveform $P_{b(RA)}$ estimated for the radial artery 44 has the same shape as that of backward-pressure-pulse-wave waveform $P_{b(AO)}$ at the heart-side end of the aorta but is advanced from the same by the propagation time Td. Therefore, the forward-pressure-pulse-wave waveform $P_{f(AO)}$ is obtained by moving the estimated forward-pressure-pulse-wave waveform $P_{f(RA)}$ by the propagation time Td in a positive direction, and the backward-pressure-pulse-wave waveform $P_{b(AO)}$ is obtained by moving the estimated backward-pressure-pulse-wave waveform $Pb_{(RA)}$ by the propagation time Td in a negative direction. The central aortic pressure waveform $P_{b(AO)}$ is continuously obtained by adding the thus obtained forward-pressure-pulse-wave waveform $P_{f(AO)}$ and backward-pressure-pulse-wave waveform $P_{b(AO)}$ to each other.

Figure 8:
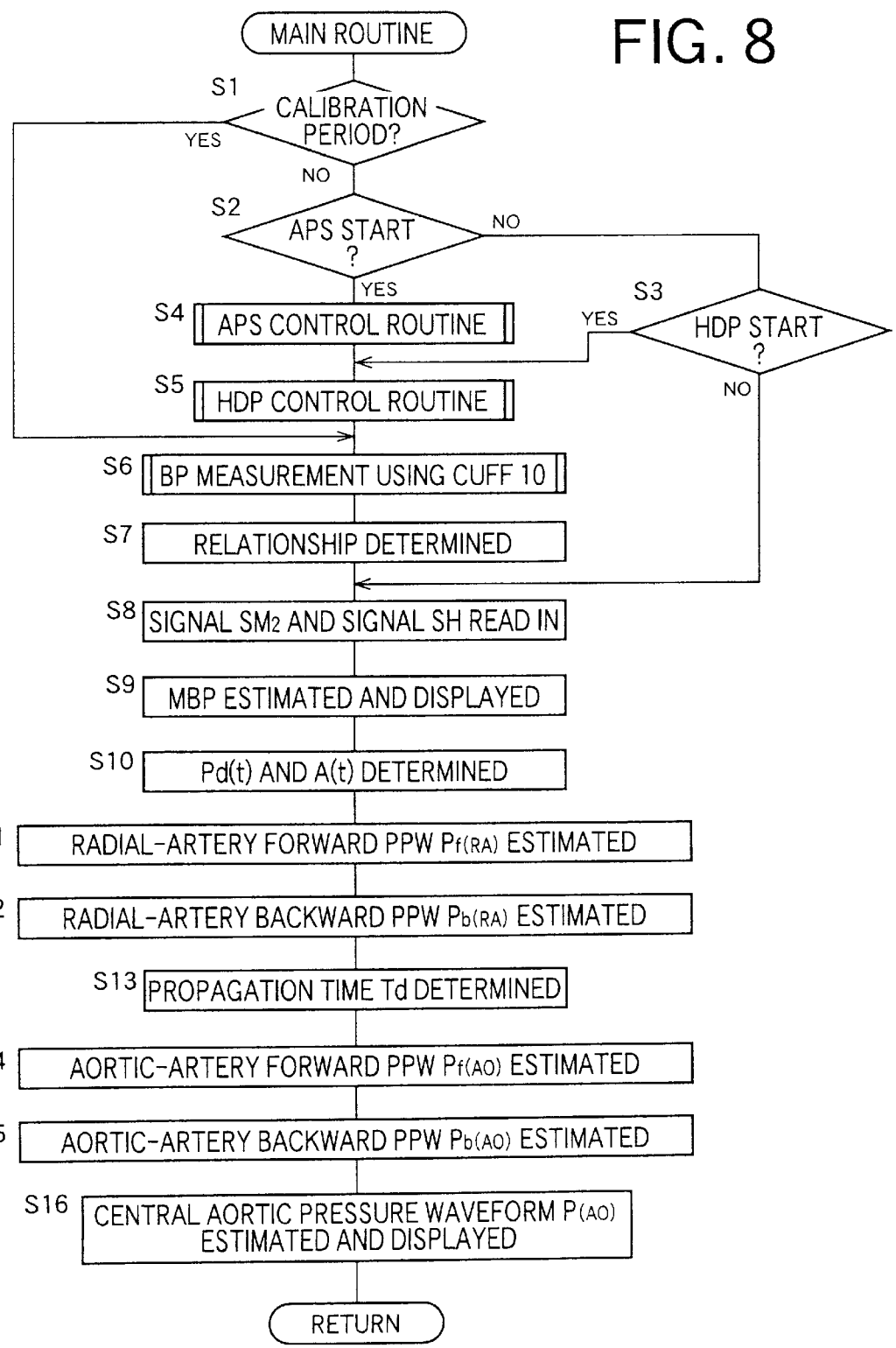
FIG. 8 is a flow chart representing a control program according to which the control device of FIG. 4 controls the apparatus of FIG. 1.

FIG. 8 is a flow chart representing a control program according to which the control device 28 controls the CAP-waveform estimating apparatus 8.

First, at Step S1, the control device 28 judges whether a time which has elapsed after the relationship is last updated at Step S7 has exceeded a predetermined calibration period (e.g., a time period from ten and several minutes to several tens of minutes). Usually, a negative judgment is made, and accordingly the control device 28 proceeds with Step S2 to judge whether a predetermined press-position changing condition (i.e., a predetermined "APS" starting condition) has been satisfied. In the present embodiment, a positive judgment is made when the active element $E_O$ of the PPW sensor 58 that detects the greatest amplitude is located in one of the opposite end portions of the array of elements E provided in the press surface 70 of the sensor 58.

For example, when the PPW detecting probe 38 is initially worn, or when the PPW sensor 58 is moved out of position relative to the radial artery 44, a positive judgment is made at Step S2. In this case, the control of the control device 28 goes to Step S4 to carry out an APS control routine. In the APS control routine, the control device 28 controls the PPW detecting probe 38 such that the active element $E_O$ of the PPW sensor 58 that produces the pulse-wave signal SM2 exhibiting the greatest amplitude is located at an optimum press position, i.e., substantially the middle of the array of elements E provided in the press surface 70 of the sensor 58. In this state, the active element $E_O$ is positioned right above the radial artery 44.

On the other hand, if the press position where the PPW sensor 58 is pressed against the radial artery 44 via the skin is in a normal range, a negative judgment is made at Step S2, so that the control goes to Step S3. At Step S3, the control device 28 judges whether a relationship updating condition or an optimum-pressing-force changing condition (i.e., a predetermined "HDP" starting condition) has been satisfied, e.g., whether such a physical motion of the subject has been detected which will change the current condition under which the PPW sensor 58 is pressed, to such an extent that will change the current relationship, shown in FIG. 6, or whether the monitor BP value MBP has significantly largely changed from the BP value measured in the last BP measurement using the cuff 10.

If a positive judgment is made at Step S3, or after Step S4 is carried out, the control goes to Step S5 corresponding to the optimum-pressing-force determining means 86. At Step S5, the control device 28 carries out an HDP control routine in which the control device 28 continuously increases the pressing force applied to the PPW sensor 58. During this pressing-force increase, the control device 28 determines, as a new optimum pressing force $P_{HDPO}$, the pressing force at which the amplitude of the pressure pulse wave $P_{(RA)}$ detected by the active element $E_O$ becomes maximum, and updates the last optimum pressing force $P_{HDPO}$ to the thus determined new one. In addition, the control device 28 maintains the pressing force applied to the sensor 58, at the thus updated, new optimum pressing force $P_{HDPO}$. In the state in which the PPW sensor 58 is pressed with the updated optimum pressing force $P_{HDPO}$, the control device 28 carries out Step S6 and the following steps.

If a positive judgment is made at Step S1 or after the control device 28 carries out Step S5, the control device 28 proceeds with Step S6 to perform a BP measurement using the cuff 10. Step S6 is followed by Step S7 to update the relationship shown in FIG. 6. More specifically described, first, at Step S6 corresponding to the BP measuring means 80, the switch valve 16 is switched to its pressure-increase position and the air pump 18 is operated, so that the air pressure in the cuff 10 is increased up to the predetermined target pressure (e.g., 180 mmHg) higher than an estimated systolic BP value of the patient, and subsequently the air pump 18 is stopped and the switch valve 16 is switched to its slow-deflation position, so that the cuff pressure is slowly decreased at the rate of 3 mmHg/sec. Based on the time-wise change of respective amplitudes of successive heartbeat-synchronous pulses of the pressure pulse wave represented by the pulse-wave signal $SM_1$ continuously obtained during this slow deflation, the control device 28 determines, according to well-known oscillometric BP determining algorithm, a systolic BP value $BP_{SYS}$, a mean BP value $BP_{MEAN}$, and a diastolic BP value $BP_{DIA}$ of the patient. The thus measured BP values are displayed on the display device 36, and then the switch valve 16 is switched to its quick-deflation position to deflate quickly the air pressure in the cuff 10.

Next, at Step S7 corresponding to the relationship determining means 88, the control device 28 newly determines a relationship between monitor BP values MBP and pressure-pulse-wave magnitude, based on the magnitudes of the pressure pulse wave $P_{(RA)}$ (i.e., the magnitudes of the pressure-pulse-wave signal $SM_2$) detected by the PPW sensor 58 and the systolic and diastolic BP values $BP_{SYS}$, $BP_{DIA}$ measured using the cuff 10 at Step S6, and update the last relationship with the thus determined new one. More specifically described, the control device 28 reads in one heartbeat-synchronous pulse of the pressure pulse wave $P_{(RA)}$ detected by the PPW sensor 58 and determines a maximum magnitude, $P_{(RA)max}$, and a minimum magnitude, $P_{(RA)min}$, of the one pulse, as illustrated in FIG. 3. Based on the thus determined maximum and minimum magnitudes $P_{(RA)max}$, $P_{(RA)min}$ and the systolic and diastolic BP values $BP_{SYS}$, $BP_{DIA}$ measured at Step S6, the control device 28 determines a relationship between monitor BP values MBP and pressure-pulse-wave magnitude $P_{(RA)}$, as shown in FIG. 6.

Step S7 is followed by Step S8 at which the control device 28 reads in a predetermined number of heartbeat-synchronous pulses (e.g., one pulse) of the pressure-pulse-wave signal $SM_2$ outputted from the active element $E_O$ of the PPW sensor 58 being pressed with the optimum pressing force $P_{HDPO}$ and a predetermined number of heartbeat-synchronous pulses (e.g., one pulse) of the heart-sound signal SH outputted from the heart-sound microphone 74.

Next, at Step S9 corresponding to the monitor-BP determining means 90, the control device 28 determines a maximum magnitude $P_{(RA)max}$ and a minimum magnitude $P_{(RA)min}$ of each pulse of the pulse-wave signal $SM_2$ read in at Step S8, and determines, according to the relationship updated at Step S7, a monitor systolic BP value $MBP_{SYS}$ and a monitor diastolic BP value $MBP_{DIA}$ of the patient based on the determined maximum and minimum magnitudes $P_{(RA)max}$, $P_{(RA)min}$, respectively. The thus determined monitor systolic and diastolic BP values $MBP_{SYS}$, $MBP_{DIA}$ are displayed on the display device 36.

At Step S10 corresponding to the BP-difference determining means 92, the control device 28 replaces, in the expressions (2) and (4), the variable $P_{(RA)}(t)$ with the continuous magnitudes forming the one pulse of the pressure-pulse-wave signal $SM_2$ that has been read in at Step S8, and gives a predetermined initial value to the variable Pd(t), and thereby determines continuous values Pd(t) and continuous values A(t) corresponding to the one pulse. In the expression (4), predetermined values, 0.0318 and 1.33, are used as the values Zc/R and C·R, respectively.

Next, the control device 28 carries out Steps S11 and S12 corresponding to the radial-artery-pressure-waveform estimating means 104. First, at Step S11, the control device 28 replaces, in the expression (6), the variable $P_{(RA)}(t)$ with the continuous magnitudes forming the one pulse of the pressure-pulse-wave signal $SM_2$ that has been read in at Step S8, and replaces the variable A(t) with the continuous values A(t) corresponding to the one pulse, determined at Step S10, and thereby estimates a continuous waveform of one pulse of a forward pressure pulse wave $P_{f(RA)}$ at the radial artery 44. Then, at Step S12, the control device 28 replaces, in the expression (7), the variable $P_{(RA)}(t)$ with the continuous magnitudes forming the one pulse of the pressure-pulse-wave signal $SM_2$ that has been read in at Step S8, and replaces the variable A(t) with the continuous values A(t) corresponding to the one pulse, determined at Step S10, and thereby estimates a continuous waveform of one pulse of a backward pressure pulse wave $P_{b(RA)}$ at the radial artery 44.

At Step S13 corresponding to the propagation-time determining means 106, the control device 28 determines, as the propagation time Td, a time difference between a time when the control device 28 finds the minimum-magnitude point of the one pulse of the pressure pulse wave $P_{(RA)}$ represented by the signal $SM_2$ read in at Step S8 and a time when the control device 28 finds the minimum-magnitude point of the first heart sound I of the one pulse of the heart-sound signal SH read in at Step S8.

Next, the control device 28 carries out Steps S14, S15 and S16 corresponding to the CAP-waveform estimating means 108. First, at Step S14, the control device 28 estimates a continuous waveform of a forward pressure pulse wave $P_{f(AO)}$ at the heart-side end of the aorta, by moving the continuous waveform of forward pressure pulse wave $P_{f(RA)}$ at the radial artery 44, estimated at Step S11, by the propagation time Td in a positive direction along the time axis. Subsequently, at Step S15, the control device 28 estimates a continuous waveform of a backward pressure pulse wave $P_{b(AO)}$ at the heart-side end of the aorta, by moving the waveform of backward pressure pulse wave $P_{b(RA)}$ at the radial artery 44, estimated at Step S12, by the propagation time Td in a negative direction along the time axis. Then, at Step S16, the control device 28 estimates a continuous waveform of a central aortic blood pressure $P_{(AO)}$ at the heart-side end of the aorta, by adding the respective waveforms of forward and backward pressure pulse waves $P_{f(AO)}$, $P_{b(AO)}$ at the heart-side end of the aorta, estimated at Steps S14 and S15, to each other. The thus estimated continuous waveform of central aortic blood pressure $P_{(AO)}$ is displayed on the display device 36.

Next, there will be described an experiment in which a CAP waveform $P_{(AO)}$ which is estimated using the vascular-system model 94, as is estimated by the CAP-waveform estimating apparatus 8, is compared with respective central aortic pressure waveforms $P_{(AO)}$ obtained in different methods.

In the experiment, first, a catheter method is employed to measure actually a central aortic pressure waveform $P_{(AO)}$ from each of eight patients who suffer arrhythmia. Second, the PPW detecting probe 38 is used to measure actually a radial-artery pressure waveform $P_{(RA)}$ from each of the same patients, and then a central aortic pressure waveform $P_{(AO)}$ of each patient is estimated, on an off-line basis, from the measured radial-artery pressure waveform $P_{(RA)}$ using a transfer function which is determined in the previously-described conventional method. Third, like the CAP-waveform estimating apparatus 8, the vascular-system model 94 is used to estimate, on an off-line basis, a central aortic pressure waveform $P_{(AO)}$ of each patient from the radial-artery pressure waveform $P_{(RA)}$ measured using the PPW detecting probe 38. The third method in which the model 94 is used differs from the illustrated embodiment in which the CAP-waveform estimating apparatus 8 is operated, only in that the third method is carried out on the off-line basis and the the estimating apparatus 8 is operated on an on-line basis. Therefore, it can be said that the CAP wave form $P_{(AO)}$ estimated using the model 94 in the third method is substantially identical with the CAP wave form $P_{(AO)}$ estimated by the estimating apparatus 8. The second, conventional method in which the transfer function is used is described in the following document: Sugimachi M, Kawada T, Shisido T, Matsumoto N, Alexander J Jr, Sunagawa K: Estimation of arterial mechanical properties from aortic and tonometric arterial pressure waveforms. Methods Inf Med 1997; 36: 250–253.

Figure 10A:
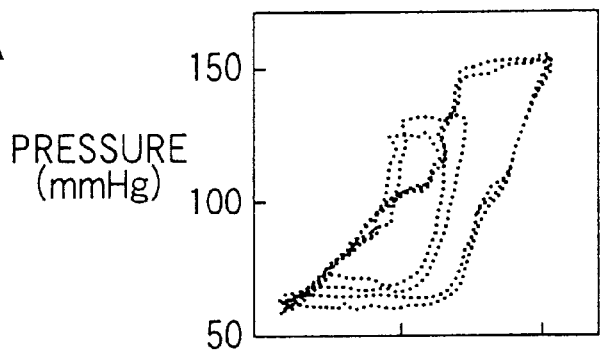
FIG. 10A is a scatter diagram of the radial-artery pressure waveform detected using the PPW detecting probe, relative to the CAP waveform detected using the catheter.
Figure 10B:
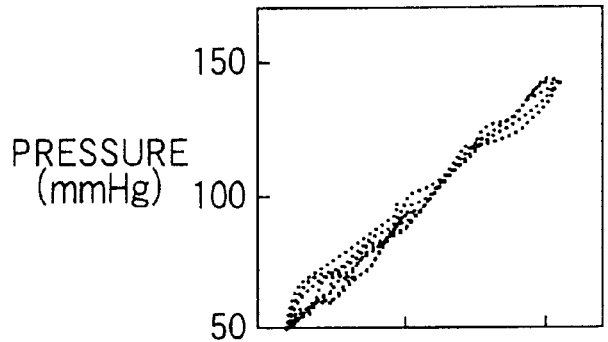
FIG. 10B is a scatter diagram of the CAP waveform estimated from the detected radial-artery pressure waveform by the conventional method using the transfer function, relative to the CAP waveform detected using the catheter.
Figure 10C:
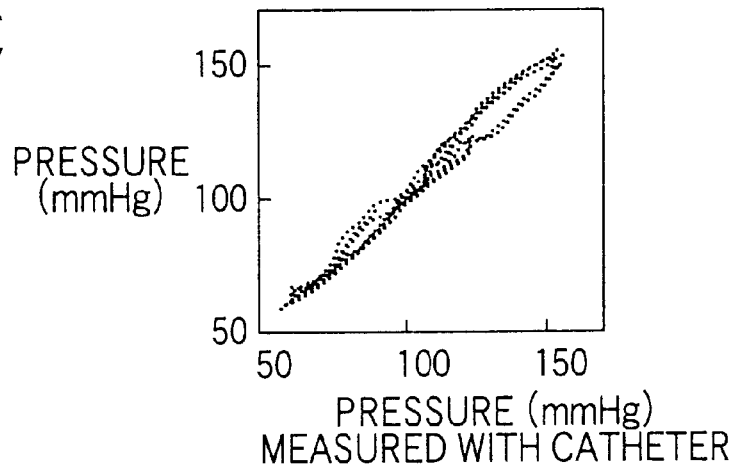
FIG. 10C is a scatter diagram of the CAP waveform estimated from the radial-artery pressure waveform by the invention method using the vascular-system model of FIG. 7, relative to the CAP waveform detected using the catheter.

FIGS. 9A, 9B, 9C, and 9D show respective CAP waveforms $P_{(AO)}$ obtained in the above-described experiment. FIG. 9A shows the CAP waveform $P_{(AO)}$ actually measured in the first, catheter method; FIG. 9B shows a radial artery pressure waveform $P_{(RA)}$ actually measured by the PPW detecting probe 38; FIG. 9C shows the CAP waveform $P_{(AO)}$ estimated from the measured radial artery pressure waveform $P_{(RA)}$ in the second, conventional method in which the transfer function is used; and FIG. 9D shows the CAP waveform $P_{(AO)}$ estimated from the measured radial artery pressure waveform $P_{(RA)}$ in the third, invention method in which the vascular-system model 94 is used. In addition, FIG. 10A shows a scatter diagram representing a relationship between the radial artery pressure waveform $P_{(RA)}$ measured by the probe 38 and the CAP waveform $P_{(AO)}$ measured in the first, catheter method; FIG. 10B shows a scatter diagram representing a relationship between the CAP waveform $P_{(AO)}$ estimated from the measured radial artery pressure waveform $P_{(RA)}$ in the second, conventional method and the CAP waveform $P_{(AO)}$ measured in the first, catheter method; and FIG. 10C shows a scatter diagram representing a relationship between the CAP waveform $P_{(AO)}$ estimated from the measured radial artery pressure waveform $P_{(RA)}$ in the third, invention method and the CAP waveform $P_{(AO)}$ measured in the first, catheter method. As is apparent from FIGS. 9A to 9D and 10A to 10C, the radial artery pressure waveform $P_{(RA)}$ measured using the probe 38, that is, the waveform $P_{(RA)}$ which is not corrected considerably differs from the CAP waveform $P_{(AO)}$ measured using the catheter, but the CAP waveform $P_{(AO)}$ estimated in each of the second, conventional method and the third, invention method considerably faithfully represents the CAP waveform $P_{(AO)}$ measured using the catheter.

Figure 11:
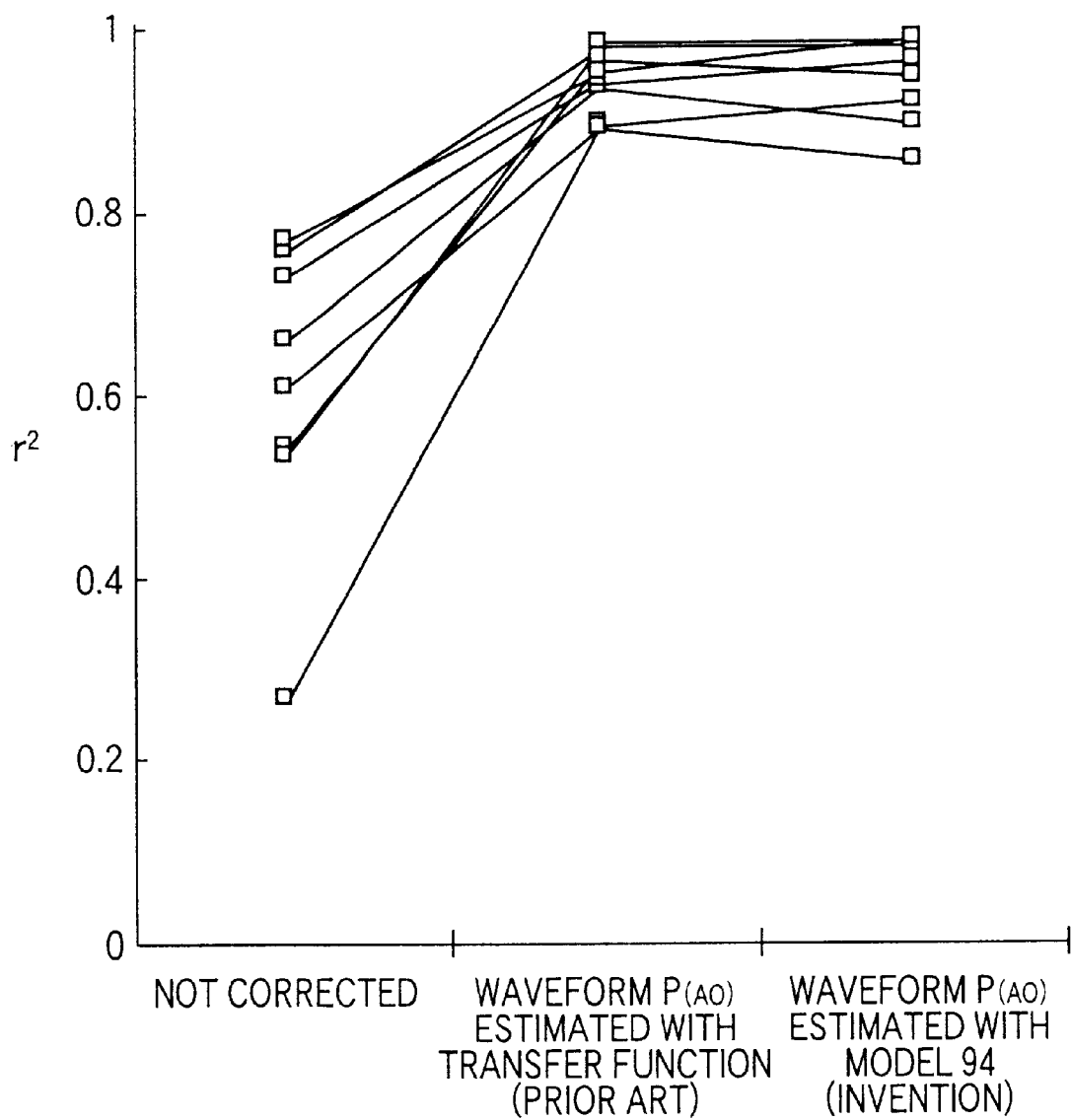
FIG. 11 is a graph showing respective correlation coefficients, $r^2$, between (A) respective CAP waveforms detected from individual patients each using the catheter and (B)(a) respective radial-artery pressure waveforms detected from the individual patients each using the PPW probe, (B)(b) respective CAP waveforms estimated from the corresponding radial-artery pressure waveforms by the conventional method using the transfer function, or (B)(c) respective CAP waveforms estimated from the corresponding radial-artery pressure waveforms by the invention method using the vascular-system model of FIG. 7.

FIG. 11 is a graph showing respective correlation coefficients, $r^2$, between (A) respective CAP waveforms $P_{(AO)}$ measured from the eight patients each using the catheter and (B)(a) respective radial-artery pressure waveforms $P_{(RA)}$ measured from the eight patients each using the PPW probe 38 (indicated in a left portion of the graph), (B)(b) respective CAP waveforms $P_{(AO)}$ estimated from the corresponding radial-artery pressure waveforms $P_{(RA)}$ by the second, conventional method using the transfer function (indicated in a middle portion of the graph), and (B)(c) respective CAP waveforms $P_{(AO)}$ estimated from the corresponding radial-artery pressure waveforms $P_{(AO)}$ in the third, invention method using the vascular-system model 94 (indicated in a right portion of the graph). FIG. 11 shows that the invention method using the model 94 can estimate a CAP waveform $P_{(AO)}$ with a high accuracy comparable with that of the conventional method using the transfer function.

It emerges from the foregoing description that in the illustrated embodiment, the BP-difference determining means 92 (Step S10) continuously determines, according to the vascular-system model 94, the BP difference A(t) between the BP $P_{(RA)}$ at the portion of the radial artery 44 pressed by the PPW sensor 58 and the BP Pd(t) at the peripheral end of the radial artery 44, based on the radial-artery pressure pulse wave $P_{(RA)}$ non-invasively and continuously measured by the PPW sensor 58; the radial-artery-pressure-waveform estimating means 104 (Steps S11, S12) continuously estimates the radial-artery forward pressure pulse wave waveform $P_{f(RA)}$ and the radial-artery backward pressure pulse wave waveform $Pb_{b(RA)}$, based on the pressure pulse wave $P_{(RA)}$ continuously measured by the PPW sensor 58 and the BP difference continuously determined by the BP-difference determining means 92 (Step S10); and the CAP-waveform estimating means 108 (Steps S14 to S16) continuously estimates the CAP waveform P(AO), based on the radial-artery forward and backward pressure pulse wave waveforms $P_{f(RA)}$ $P_{b(RA)}$ and the propagation time Td successively determined by the propagation-time determining means 106 (Step S13). Thus, the CAP-waveform estimating apparatus 8 can continuously estimate the CAP waveform $P_{(AO)}$, with accuracy and ease, by just measuring continuously the radial-artery pressure waveform $P_{(RA)}$ and the propagation time Td.

While the present invention has been described in its preferred embodiment, it is to be understood that the invention may otherwise be embodied.

For example, in the illustrated CAP-waveform estimating apparatus 8 has the function of non-invasively and continuously estimating the BP of a living subject. However, the apparatus 8 may be so modified as not to have the function. In the latter case, the cuff 10 may be omitted.

In addition, in the illustrated embodiment, the heart-sound microphone 74 which detects the heart sounds of the subject is employed as the first sensor. However, a carotid-pulse-wave sensor which detects a pulse wave from a carotid artery of the subject may be employed in place of the microphone 74.

Moreover, in the illustrated embodiment, the PPW detecting probe 38 is worn on the wrist 54 of the subject so that the PPW sensor 58 presses the radial artery 44 via the body surface or skin 52 and detects the radial-artery pressure waveform $P_{(RA)}$ as a sort of peripheral-artery pressure waveform. However, since the carotid artery is located on a distal side of the central aorta, the probe 38 may be so modified as to be worn on the neck of the subject and detect a carotid-artery pressure waveform as a sort of peripheral-artery pressure waveform.

It is to be understood that the present invention may be embodied with other changes, modifications and improvements which may occur to a person skilled in the art, without departing from the spirit and scope of the invention defined in the appended claims.

What is claimed is:

1. An apparatus for non-invasively estimating a waveform of a blood pressure in a central artery of a living subject, comprising:
    a pressure-pulse-wave detecting device which includes a pressure-pulse-wave sensor adapted to be pressed, via a skin of the subject, against a first portion of a peripheral artery located on a downstream side of the central artery and which non-invasively detects, through the pressure-pulse-wave sensor, a pressure pulse wave produced from the first portion of the peripheral artery;
    a blood-pressure-difference determining means for determining, according to a predetermined vascular-system model, a blood-pressure difference between a blood pressure at the first portion of the peripheral artery pressed by the pressure-pulse-wave sensor and a blood pressure at an end of the peripheral artery, based on the pressure pulse wave detected by the pressure-pulse-wave detecting device;
    a peripheral-artery-blood-pressure-waveform estimating means for estimating, based on the pressure pulse wave detected by the pressure-pulse-wave detecting device and the blood-pressure difference determined by the blood-pressure-difference determining means, a waveform of a forward pressure pulse wave at the first portion of the peripheral artery pressed by the pressure-pulse-wave sensor, and a waveform of a backward pressure pulse wave at the first portion of the peripheral artery;
    a propagation-time determining means for determining a propagation time in which the pressure pulse wave propagates from a second portion of the central artery to the first portion of the peripheral artery; and
    a central-artery-blood-pressure-waveform estimating means for estimating, based on the respective waveforms of the forward and backward pressure pulse waves estimated by the peripheral-artery-blood-pressure-waveform estimating means and the propagation time determined by the propagation-time determining means, a waveform of a forward pressure pulse wave at the second portion of the central artery and a waveform of a backward pressure pulse wave at the second portion of the central artery, and estimating a waveform of a blood pressure at the second portion of the central artery, by adding the respective estimated waveforms of the forward and backward pressure pulse waves at the second portion of the central artery.

2. An apparatus according to claim 1, wherein the pressure-pulse-wave sensor comprises a radial-pressure-pulse-wave sensor which is adapted to be pressed, via the skin of the subject, against a radial artery that is located on the downstream side of the central artery, and the pressure-pulse-wave detecting device non-invasively detects, through the radial-pressure-pulse-wave sensor, a radial pressure pulse wave, $P_{(RA)}(t)$, produced from the radial artery at a time, t.

3. An apparatus according to claim 2, wherein the blood-pressure-difference determining means comprises determining means for determining, according to the predetermined vascular-system model, a blood-pressure difference, $A(t+T)$, between a blood pressure in the radial artery pressed by the radial-pressure-pulse-wave sensor and a blood pressure, $Pd(t+T)$, at said end of the peripheral artery, based on the radial pressure pulse wave $P_{(RA)}(t+T)$ detected by the pressure-pulse-wave detecting device, at a time, T, after said time t, according to a following expression:

$$A(t+T)=P_{(RA)}(t+T)-Pd(t+T).$$

4. An apparatus according to claim 3, wherein the blood-pressure-difference determining means further comprises estimating means for estimating, according to the predetermined vascular-system model, said blood pressure $Pd(t+T)$ at said end of the peripheral artery, at said time T after said time t, according to a following expression:

$$Pd(t+T)=Pd(t)+\{A(t)/C_1/C_2-Pd(t)/C_2\}\times T$$

where
    $C_1$ and $C_2$ are predetermined constants; and
    $Pd(t)$ is a predetermined initial value.

5. An apparatus according to claim 4, wherein the peripheral-artery-blood-pressure-waveform estimating means comprises radial-artery-blood-pressure-waveform estimating means for estimating, based on the radial pressure pulse wave $P_{(RA)}(t+T)$ detected by the pressure-pulse-wave detecting device and the blood-pressure difference $A(t+T)$ determined by the blood-pressure-difference determining means, a waveform, $P_{f(RA)}(t+T)$, of a forward radial pressure pulse wave at the radial artery pressed by the radial-pressure-pulse-wave sensor, and a waveform, $P_{b(RA)}(t+T)$ of a backward radial pressure pulse wave at the radial artery, according to two following expressions, respectively:

$$P_{f(RA)}(t+T)=(P_{(RA)}(t+T)+A(t+T))/2$$

$$P_{b(RA)}(t+T)=(P_{(RA)}(t+T)-A(t+T))/2.$$

6. An apparatus according to claim 4, wherein the predetermined vascular-system model comprises:
    a first resistor which represents a portion of the peripheral artery that is located between the radial artery pressed by the radial-pressure-pulse-wave sensor and said end of the peripheral artery and which has an impedance, Zc;
    a second resistor which is connected in series to the first resistor and which has a resistance, R; and
    a capacitor which is connected in series to the first resistor and in parallel to the second resistor and which has a capacitance, C,
    wherein said constant $C_1$ is equal to a quotient, Zc/R, obtained by dividing the impedance Zc by the resistance R, and said constant $C_2$ is equal to a product, C·R, of the capacitance C and the resistance R.

7. An apparatus according to claim 1, further comprising a central-pulse-wave detecting device which detects a central pulse wave, SH, which is produced from said second portion of the central artery, wherein the propagation-time determining means comprises means for determining, as said propagation time, a time difference between a first time when the central-pulse-wave detecting device detects a characteristic point on the central pulse wave SH detected from said second portion of the central artery and a second time when the pressure-pulse-wave detecting device detects a corresponding characteristic point on the pressure pulse wave $P_{(RA)}$ detected from said first portion of the peripheral artery.

8. An apparatus according to claim 5, wherein the central-artery-blood-pressure-waveform estimating means comprises:

means for estimating said waveform, $P_{f(AO)}(t+T)$, of the forward pressure pulse wave at said second portion of the central artery, by moving said waveform $P_{f(RA)}(t+T)$ of the forward radial pressure pulse wave estimated by the radial-artery-blood-pressure-waveform estimating means by said propagation time in a positive direction along an axis indicative of said time t;

means for estimating said waveform, $P_{b(AO)}(t+T)$, of the backward pressure pulse wave at said second portion of the central artery, by moving said waveform $P_{b(RA)}(t+T)$ of the backward radial pressure pulse wave estimated by the radial-artery-blood-pressure-waveform estimating means by said propagation time in a negative direction along said axis indicative of said time t; and means for estimating said waveform, $P_{(AO)}(t+T)$, of the blood pressure at said second portion of the central artery, by adding the respective estimated waveforms $P_{f(AO)}(t+T)$, $P_{b(AO)}(t+T)$, of the forward and backward pressure pulse waves at said second portion of the central artery.

* * * * *